(12) United States Patent
Schäfer et al.

(10) Patent No.: US 9,861,419 B2
(45) Date of Patent: Jan. 9, 2018

(54) DEVICE FOR HANDLING A BONE SCREW

(71) Applicant: Silony Medical International AG, Frauenfeld (CH)

(72) Inventors: Bernd Schäfer, Plochingen (DE); Henry Halm, Neustadt (DE)

(73) Assignee: SILONY MEDICAL INTERNATIONAL AG, Frauenfeld (CH)

( * ) Notice: Subject to any disclaimer, the term of this patent is extended or adjusted under 35 U.S.C. 154(b) by 370 days.

(21) Appl. No.: 14/257,404

(22) Filed: Apr. 21, 2014

(65) Prior Publication Data
US 2014/0316423 A1      Oct. 23, 2014

(30) Foreign Application Priority Data

Apr. 20, 2013 (DE) .................. 10 2013 207 183

(51) Int. Cl.
*A61B 17/70*    (2006.01)
*A61B 17/88*    (2006.01)
(Continued)

(52) U.S. Cl.
CPC ...... *A61B 17/8875* (2013.01); *A61B 17/7086* (2013.01); *A61B 17/7091* (2013.01);
(Continued)

(58) Field of Classification Search
CPC .......... A61B 2090/031; A61B 17/7091; A61B 17/8875; A61B 17/7086; A61B 17/7032; A61B 17/7083; A61B 17/7076; A61B 17/7088; A61B 17/7082; A61B 17/708; A61B 17/8886; A61B 17/8888; A61B 17/8891; B25B 7/00; B25B 7/12; B25B 7/14
(Continued)

(56) References Cited

U.S. PATENT DOCUMENTS 7,824,413 B2 * 11/2010 Varieur ............. A61B 17/7086
                                                          606/104
7,887,541 B2 *  2/2011 Runco ................ A61B 17/7086
                                                          606/279
(Continued)

FOREIGN PATENT DOCUMENTS

DE   202011102890 U1   1/2012
EP         1694226 B1   6/2005

*Primary Examiner* — Tatiana Nobrega
*Assistant Examiner* — Marcela I Shirsat
(74) *Attorney, Agent, or Firm* — Henry M. Feiereisen LLC

(57) ABSTRACT

A device for handling a bone screw to be connected with a vertebral rod includes an essentially cylindrical and hollow housing and an adjustment tool which axially traverses the housing and which has a section provided with an outer threading and is screwed into an internal threading of the housing, wherein the housing is constructed pliers-like and has a first and a second jaw which relative to the user each have a proximal and a distal end, wherein the distal ends engage at the head of the bone screw, wherein the two jaws are pivotably connected with each other via a pivot axis which is situated between the distal and proximal ends and extends orthogonally in relation to the longitudinal axis of the housing, and wherein the internal threading of the housing is provided on a proximal end of a single one of the jaws.

9 Claims, 4 Drawing Sheets

(51) Int. Cl.
  *B25B 7/14* (2006.01)
  *B25B 7/12* (2006.01)
  *B25B 7/00* (2006.01)
  *A61B 90/00* (2016.01)

(52) U.S. Cl.
  CPC ........... *A61B 2090/031* (2016.02); *B25B 7/00* (2013.01); *B25B 7/12* (2013.01); *B25B 7/14* (2013.01)

(58) Field of Classification Search
  USPC .......... 606/104; 81/326, 327, 334, 345, 355, 81/358
  See application file for complete search history.

(56) References Cited

U.S. PATENT DOCUMENTS

| | | |
|---|---|---|
| 2003/0225408 A1 | 12/2003 | Nichols |
| 2006/0079909 A1 | 4/2006 | Runco |
| 2006/0293692 A1* | 12/2006 | Whipple ............ A61B 17/7032 606/104 |
| 2008/0154277 A1 | 6/2008 | Machalk et al. |
| 2012/0253413 A1 | 10/2012 | Runco |

* cited by examiner

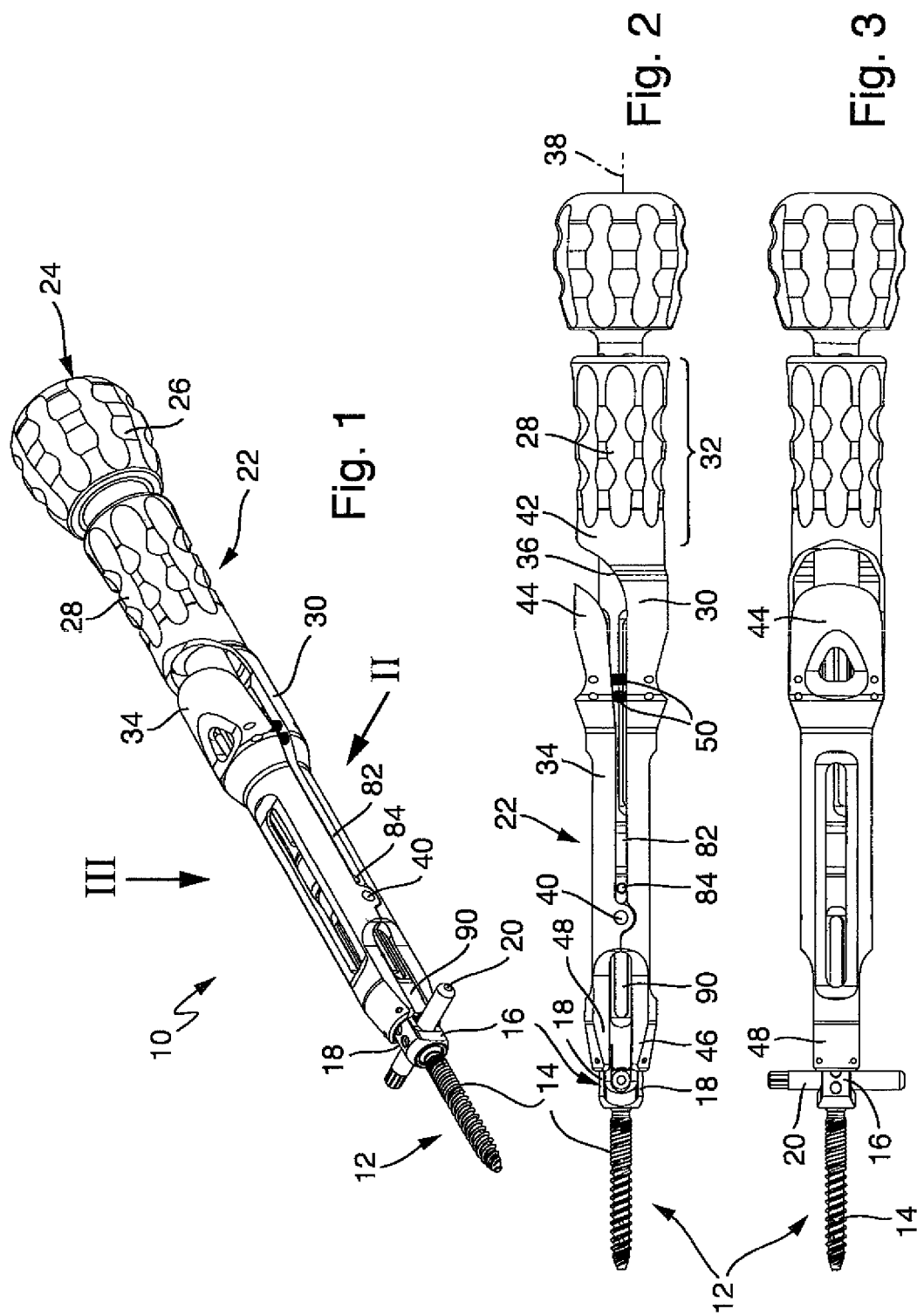

DEVICE FOR HANDLING A BONE SCREW

CROSS-REFERENCES TO RELATED APPLICATIONS

This application claims the priority of German Patent Application, Serial No. 10 2013 207 183.3, filed Apr. 20, 2013, pursuant to 35 U.S.C. 119(a)-(d), the disclosure of which is incorporated herein by reference.

BACKGROUND OF THE INVENTION

The present invention relates to a device for handling a bone screw.

The following discussion of related art is provided to assist the reader in understanding the advantages of the invention, and is not to be construed as an admission that this related art is prior art to this invention.

A device of this type is known from EP 1 694 226 B1. This device serves for connecting a bone screw, which is anchored in a bone, in particular a vertebra, with a vertebral rod. For this purpose the bone screw has a forked head into which the vertebral rod is inserted and where it is fixed by means of a grub screw or by means of a cap nut. In order to join the forked head with the vertebral rod, a device is required with which the vertebral rod is inserted or slid between the two legs of the fork head. The device is constructed in the manner of pliers and has two jaws whose proximate ends face toward the user and whose distal ends engage on the head of the bone screw. The two jaws are articulately or pivotally interconnected via a transverse axis so that a pushing together of the proximal ends causes an opening of the distal ends so that the bone screw can be grasped.

In order to move the vertebral rod in the direction of the fork head of the bone screw, an adjustment tool is provided which is screwed between the two jaws. For this the adjustment tool has a section with an outer threading, which is screwed into an internal threading provided on the insides of the two jaws. A disadvantage is that the internal threading is configured as two threading halves, as a result of being provided on the two insides of the jaws. On one hand the manufacture of the internal threading is relative work intensive because after assembling the two jaws the threadings, in particular their transition from one jaw to the other jaw, has to be in perfect alignment, on the other hand the support of the jaws for pivoting relative to each other causes a relatively great play between the internal threading of the jaws and the outer threading of the adjustment tool.

It would therefore be desirable and advantageous to provide an improved device in which the adjustment tool is guided more precisely in the housing of the device.

SUMMARY OF THE INVENTION

According to one aspect of the present invention, a device for handling a bone screw to be connected with a vertebral rod includes: an essentially cylindrical and hollow housing constructed pliers-like and having a first jaw and a second jaw which relative to the user each have a proximal and a distal end, wherein the distal ends engage at a head of the bone screw, wherein the two jaws are pivotably interconnected via a pivot axis which is situated between the distal and proximal ends and extends orthogonally in relation to a longitudinal axis of the housing, wherein an internal threading of the housing is provided on the proximal end of a single one of the first and second jaws; and an adjustment tool axially traversing the housing, wherein the adjustment tool has a section provided with an outer threading and is threadably engaged in the internal threading of the housing.

According to the invention, the device is formed by a housing, which is essentially formed by a jaw in which the internal threading is provided, and into which the adjustment tool is screwed with its outer threading. On this housing a jaw is pivotally connected so that the head of the bone screw can be grasped with this jaw. In the region outside of the section provided with the internal threading the housing is also configured as a jaw and together with the other jaw serves as grasping tool.

A simple releasing and grasping of the head of the bone screw is achieved in that the two jaws do not cross over. This achieves that when the proximal ends of the two jaws are pushed together, the distal ends open and the head of the bone screw can be received. In addition the mounting of the jaws according to the invention is significantly simpler than in the case of jaws which cross over.

According to another advantageous feature of the invention, one jaw may be fixed relative to the longitudinal axis of the internal threading and the other jaw is pivotal. The fixed jaw thus forms the housing or is part of the housing of the device and carries the internal threading for the adjustment tool.

According to the invention the jaw carrying the internal threading protrudes over the other jaw in axial direction in particular with its internal threading. The other jaw is inserted in a recess of the fixed jaw and thus completes the sheath of the fixed jaw. This recess has no threading.

According to another advantageous feature of the invention, the adjustment tool is constructed at least two-part in axial direction and has a rotatable section which is provided with the outer threading and a rotatively fixed section which engages on the vertebral rod. In this way the rotating movement of the adjustment tool with which the adjustment tool is screwed into the housing of the device, is not transmitted to the vertebral rod but merely into the axial displacement of the adjustment tool inside the housing of the device. The vertebral rod is thus carefully urged onto the fork head. The two sections of the adjustment tool are rotatable relative to each other but cannot be detached from each other.

According to another advantageous feature of the invention, the rotatively fixed section is guided in longitudinal direction between the two jaws. For this the rotatively fixed section has for example two pins which project radially outwardly and engage between the two jaws and prevent a rotation of the rotatively fixed section relative to the housing.

According to another advantageous feature of the invention, the one jaw engages in the turns of the outer threading of the adjustment tool when the proximal ends of the jaws are pushed together. When the adjustment tool is not yet screwed into the housing to the degree that its outer threading protrudes over or out of the internal threading, the movable jaw can still be pushed inwardly, i.e., the bone screw can be grasped at its head with the device. When the adjustment tool is further screwed into the internal threading of one of the jaws and the outer threading protrudes over the internal threading in distal direction, the adjustment tool blocks the two jaws from being pushed together, in particular the proximal end of the movable jaw can no longer be pushed in because it abuts on the internal threading of the adjustment tool. As a result, the two jaws can no longer be pushed together so that the bone screw is securely held by the device. An inadvertent release of the bone screw from the device is thus prevented.

According to another advantageous feature of the invention, the adjustment tool is configured hollow and the hollow body has a diameter which essentially corresponds to the outer diameter of the head of the bone screw. The adjustment tool has a wall thickness which essentially corresponds to the two legs of the fork head so that a grub screw can be screwed through the adjustment tool between the two legs into the fork head of the bone screw and thereby the vertebral rod fixed in the head of the bone screw.

According to another advantageous feature of the invention, the outer threading of the adjustment tool has a diameter that is greater than the internal threading of or the distance between the pushed together proximal ends of the jaws. As mentioned this prevents the two proximal ends of the jaws from being inadvertently pushed together when the adjustment tool is screwed into the housing. An inadvertent release of the bone screw from the device is thus not possible.

According to another advantageous feature of the invention, the housing and/or the adjustment tool has receptacles for additional holding and/or turning handles. With these holding and turning handles the lever can be increased on one hand for holding and on the other hand for operating the device and as a result the device can be operated more sensitively.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 1 is a perspective view of the device in a position during use;

FIG. 2 is a side view of the device taken in the direction of the arrow II according to FIG. 1;

FIG. 3 is a top view onto the device taken in the direction of the arrow III according to FIG. 1;

DETAILED DESCRIPTION OF PREFERRED EMBODIMENTS

Figure 4:
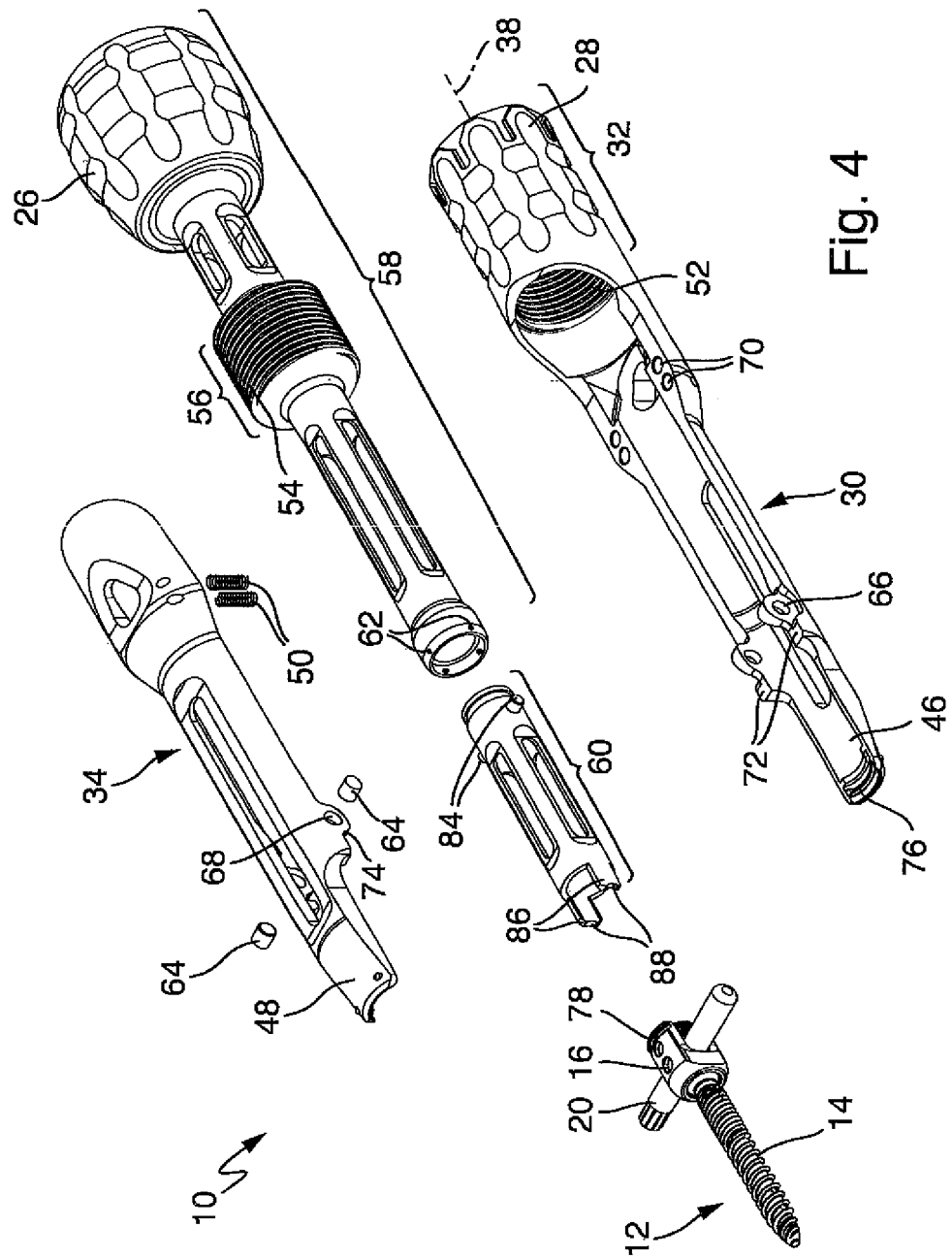
FIG. 4 is an exploded perspective view of the device.

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a device overall designated with reference numeral 10 with which a bone screw 12 can be grasped. In the shown exemplary embodiment this bone screw 12 is configured as polyaxial screw with a screw shaft 14 and a fork head 16. This fork head 16 has two parallel legs 18 which embrace a vertebral rod 20. The device 10 has a housing 22 which is axially traversed by an adjustment tool 24. An integrated turn handle is located on the adjustment tool 24, with which the adjustment tool 24 can be rotated in the housing 22. The housing 22 is held on an integrated holding handle 28.

As can be seen form FIG. 2 the housing 22 is essentially constructed two-part and has a first jaw 30 which has a section on which the holding handle 28 is formed. The housing 22 is completed by a second jaw 34 which is fitted into a recess 36 of the first jaw 30. The two jaws 30 and 34 are articulately interconnected via a pivot bearing 40 which extends transverse to the longitudinal axis 38, so that when pushing the two proximal ends 42 and 44 together, whereby in particular the proximal end 44 is pushed into the recess 36, the distal ends 46 and 48 move apart from each other so that the fork head 16 can be pushed between the two distal ends 46 and 48. In the region of the proximal ends 42 and 44 restoring springs 50 are arranged which urge the two proximal ends 42 and 44 back into their starting position. As can be easily seen from FIGS. 1 to 3, the instrument 10 is operated with one hand in that the handle 28 is held with four fingers and the proximal end 44 is operated, in particular pushed in, with the thumb of this hand. In this way the fork head 16 of the bone screw 12 is grasped.

FIG. 4 shows the device 10 in its individual parts and an internal threading 52 in the section 32 of the first jaw 30, i.e., in the handle 28, can be recognized. An outer threading 54 is screwed into this internal threading 52, which outer threading 54 is provided on a section 56 of the adjustment tool 24.

It can further be recognized that the adjustment tool 24 is constructed two-part and has a first section 58 which has the outer threading 54, and a second section 60 which are interconnected so that they can be rotated relative to each other, but are non-detachable in axial direction. This occurs by way of a press-fit stem of which press-fit stem points 62 can be recognized. The pivot bearing 40 is formed by two bearing bolts 64, which engage in the corresponding receptacles 66 and 68 in the two jaws 30 and 34. The restoring springs 50 are supported in indentations 70. An end position of the two jaws 30 and 34 is achieved via stops 72 and 74, which prevent the distal ends 46 and 48 to pivot into a fully closed position. These ends 46 and 48 have circumferential grooves 76 in the internal surface for grasping an indentation 78 in the fork head 16 of the bone screw 12.

When the two jaws 30 and 34 are joined, as shown in FIGS. 1 and 2, a longitudinal slot 82 forms between these two jaws 30 and 34, into which pins 84 which radially protrude from the second section 60 engage. These pins 84 prevent a rotation of this second section 60 so that the latter can only be moved in the direction of the longitudinal axis 38. The first section 58 on the other hand is guided so as to be screwable in the first jaw 30.

On the distal end of the second section 60 two extensions 86 are located which on their free ends each have an indentation 88 with which the vertebral rod 20 can be pushed in the direction of the fork head 16. This vertebral rod 20 is displaceable within a longitudinal slot 90 (see FIGS. 1 and 2) which is also formed between the two jaws 30 and 34, and is moved during screwing in of the adjustment tool 24 in the direction of the bone screw 12.

Figure 5:
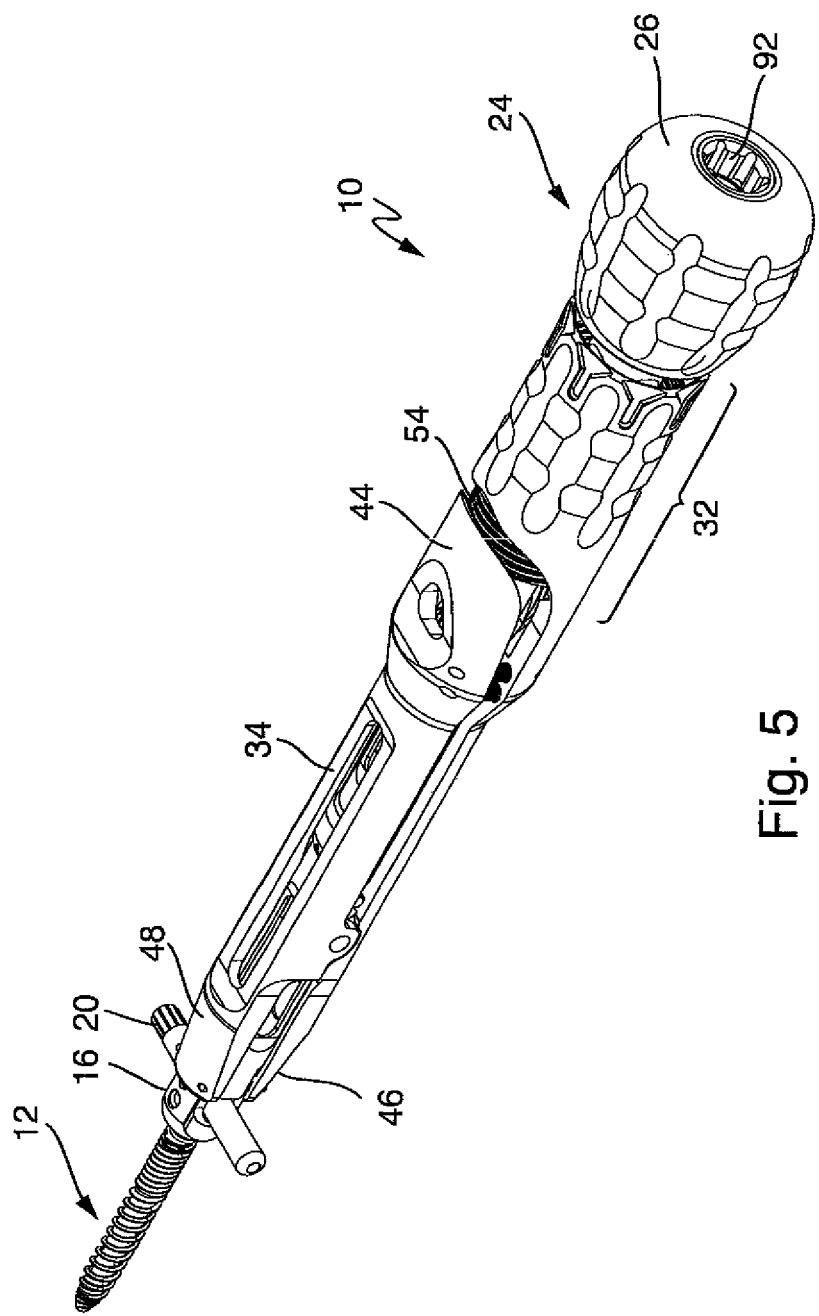
FIG. 5 is a perspective view of the device with completely screwed in adjustment tool.

In FIG. 5 the adjustment tool 24 is further screwed in than in FIG. 1. It can be seen that the outer threading 54 axially protrudes out of the section 32 in which the internal threading 52 is provided, so that the outer threading 54 reaches the pivot region of the proximal end 44 of the second jaw 34. This jaw 34 can no longer be actuated, in particular the proximal end 44 can no longer be pushed in so that there is no risk that the fork head 16 of the bone screw 12 detaches from the distal ends 46 and 48, i.e., from the device 10. When the adjustment tool 24 is screwed in, the bone screw 12 is thus secured on the device 10.

A grub screw can then be inserted in the direction of the longitudinal axis 38 via the central opening in the handle 28 by means of a suitable tool and screwed into the fork head 16 and with this the vertebral rod 20 can be fixed on the bone screw 12.

Figure 6:
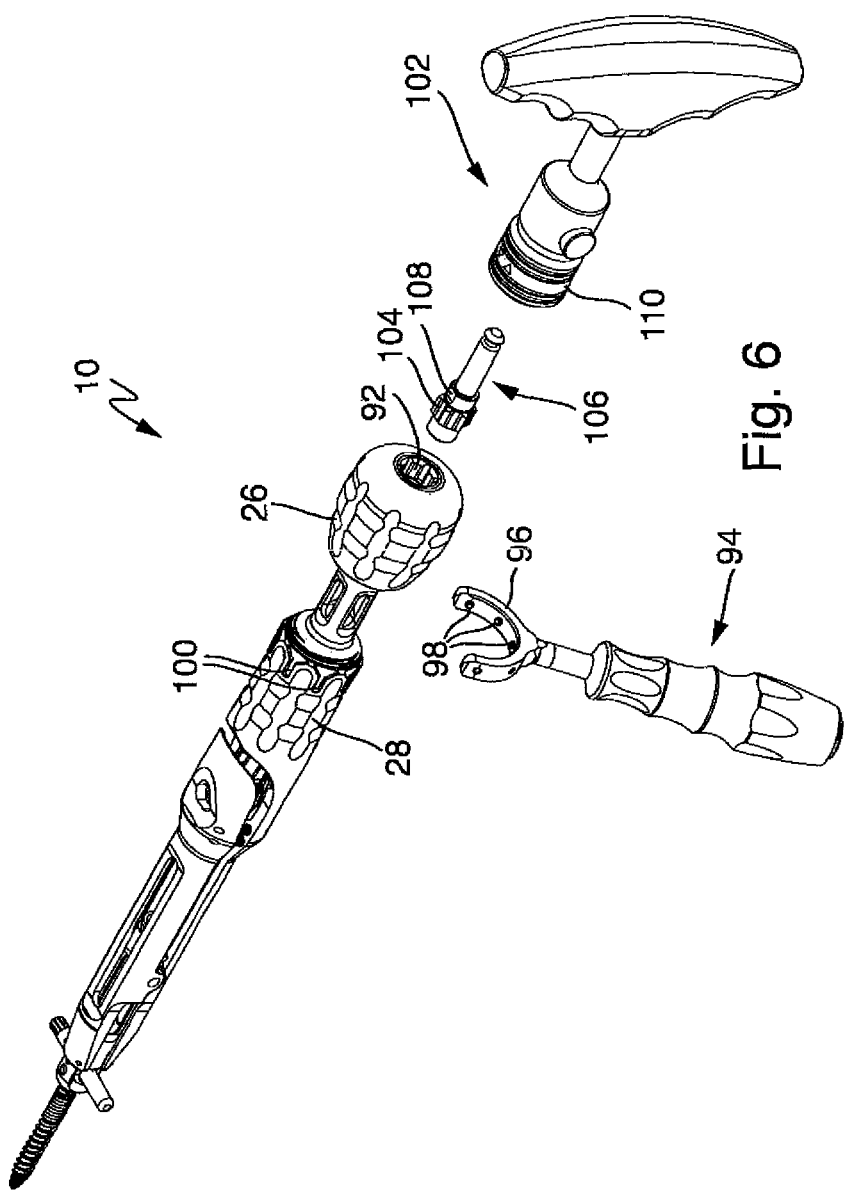
FIG. 6 is a perspective representation of the device with additional holding and turn handles.

In the case greater forces or exact torques have to be exerted, the device 10 can be equipped with additional external tools as shown in FIG. 6. On one hand an additional external handle 94 can be fastened on the handle 25 in that a receiving fork 96 with inwardly protruding pins 98 is pushed onto the handle 28 so that the pins 98 engage pin receptacles 100 which are axially open in the direction of the proximal end 42 and are distributed over the circumference.

In addition the turn handle 26 can be provided with an external turn handle 102 in that an adapter 106 which has a toothing 104 is inserted into the central opening 92, onto which adapter 106 the turn handle 102 is pushed, which can be form fittingly connected at flanks 108 with the adapter. The turn handle 102 has a torque limiter 110 and can be switched from left turning to right turning.

With the device 10 according to the invention a bone screw 12 can be connected to a vertebral rod in a simple manner.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated. What is claimed as new and desired to be protected by Letters Patent is set forth in the appended claims and includes equivalents of the elements recited therein:

What is claimed as new and desired to be protected by Letters Patent is set forth in the appended claims and includes equivalents of the elements recited therein:

1. A device for handling a bone screw to be connected with a vertebral rod comprising:
    an essentially cylindrical and hollow housing constructed pliers-like and having a first jaw and a second jaw which relative to the user each have a proximal and a distal end, said distal ends engaging at a head of the bone screw, wherein the two jaws are pivotably interconnected via a pivot axis which is situated between the distal and proximal ends and extends orthogonally in relation to a longitudinal axis of the housing, wherein an internal threading of the housing is provided on the proximal end of the first jaw but not the second jaw, said internal threading being defined by a radius; and
    an adjustment tool axially traversing the housing, said adjustment tool having a section provided with an outer threading and being threadably engaged in the internal threading of the housing,
    said adjustment tool being movable between a first position in which the external threading is positioned proximal to the proximal end of the second jaw and a second position in which at least a portion of the external threading axially coincides with the proximal end of the second jaw
    wherein in the first position the proximal end of the second jaw is pivotable into a position radially inwardly relative to the internal threading thereby causing the distal ends to move apart from each other for receiving a head of the bone screw, and
    wherein in the second position the at least one portion of the external threading prevents inward pivoting of the proximal end of the second jaw.

2. The device of claim 1, wherein in relation to a longitudinal axis of the internal threading the first jaw is rigid and the second jaw is pivotable.

3. The device of claim 1, wherein the first jaw protrudes over the second jaw in axial direction.

4. The device of claim 1, wherein the first jaw protrudes over the second jaw in axial direction with its internal threading.

5. The device of claim 1, wherein the adjustment tool is constructed at least two-part in axial direction and has a rotatable section which is provided with the outer threading and a rotatively fixed section which engages on the vertebral rod.

6. The device of claim 5, wherein the rotatively fixed section is guided in longitudinal direction between the first and second jaws.

7. The device of claim 1, wherein the adjustment tool is constructed as a hollow body which has an outer diameter essentially corresponding to an outer diameter of the head of the bone screw.

8. The device of claim 1, wherein the outer threading of the adjustment tool has a diameter which is greater than the internal diameter of the proximal ends or greater than a distance between the proximal ends in a pushed-together state of the first and second jaws.

9. The device of claim 1, wherein the housing and/or the adjustment tool has receptacles for additional holding and/or turn handles.

* * * * *